(12) United States Patent
Goode

(10) Patent No.: US 7,225,025 B2
(45) Date of Patent: May 29, 2007

(54) MULTIPLEXED MEDICAL DEVICE LEAD WITH STANDARD HEADER

(75) Inventor: Paul V. Goode, Santa Clarita, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 124 days.

(21) Appl. No.: 10/955,854

(22) Filed: Sep. 30, 2004

(65) Prior Publication Data

US 2005/0043768 A1 Feb. 24, 2005

Related U.S. Application Data

(62) Division of application No. 10/008,529, filed on Nov. 7, 2001, now Pat. No. 6,859,667.

(51) Int. Cl.
*A61N 1/00* (2006.01)

(52) U.S. Cl. .................................................. 607/28

(58) Field of Classification Search ............ 607/17–24, 607/28
See application file for complete search history.

(56) References Cited

U.S. PATENT DOCUMENTS

| | | | |
|---|---|---|---|
| 4,432,372 A | 2/1984 | Monroe et al. | 128/675 |
| 4,485,813 A | 12/1984 | Anderson et al. | 128/675 |
| 4,566,456 A | 1/1986 | Koning et al. | 128/419 |
| 4,708,143 A | 11/1987 | Schroeppel | 128/419 |
| 4,791,935 A | 12/1988 | Baudino et al. | 128/637 |
| 4,967,755 A | 11/1990 | Pohndorf et al. | 128/675 |
| 5,275,171 A | 1/1994 | Barcel | 607/122 |
| 5,324,326 A | 6/1994 | Lubin | 607/122 |
| 5,336,253 A | 8/1994 | Gordon et al. | 607/122 |
| 5,411,532 A | 5/1995 | Mortazavi | 607/22 |
| 5,431,692 A * | 7/1995 | Hansen et al. | 607/28 |
| 5,651,767 A | 7/1997 | Schulman et al. | 604/8 |
| 5,660,163 A | 8/1997 | Schulman et al. | 126/635 |
| 5,728,281 A | 3/1998 | Holmstrom et al. | 204/403 |
| 5,843,135 A | 12/1998 | Weijand et al. | 607/17 |

(Continued)

OTHER PUBLICATIONS

"Low-Profile Connector for Implantable Cardiac Pacemakers", The European Standard EN 50077; The British Standard Published under the authority of the Standards Board,(1993), 15 pages.

(Continued)

*Primary Examiner*—George Manuel
(74) *Attorney, Agent, or Firm*—Schwegman, Lundberg, Woessner, & Kluth, P.A.

(57) ABSTRACT

Systems and methods for providing a cardiac stimulus device lead with additional sensing capabilities without violating header standards is disclosed. A cardiac stimulus device lead is provided according to one aspect. According to one embodiment, the lead includes a first conductor and a second conductor for transmitting an electrical pulse from a pulse generator. The lead further includes a multiplexer switch, a first electrode, a second electrode, a sensing circuit and a controller. The first conductor is connected to the multiplexer switch. A first terminal of the multiplexer switch is connected to the first electrode and a second terminal of the multiplexer switch is connected to the sensing circuit. The second conductor is connected to the second electrode. The controller is connected to the multiplexer switch, and is adapted to selectively connect the first conductor to one of the first electrode and the sensing circuit.

36 Claims, 18 Drawing Sheets

U.S. PATENT DOCUMENTS

| | | | | |
|---|---|---|---|---|
| 5,999,848 | A | 12/1999 | Gord et al. | 607/2 |
| 6,043,437 | A | 3/2000 | Schulman et al. | 174/258 |
| 6,221,012 | B1 | 4/2001 | Maschke et al. | 600/301 |
| 6,223,081 | B1 | 4/2001 | Kerver | 607/17 |
| 2003/0088303 | A1 | 5/2003 | Goode | 607/122 |

OTHER PUBLICATIONS

Carr, W. N., et al., "Integrated Pressure Sensor With Remote Power Source and Remote Readout", *The 8th International Conference on Solid-State Sensors and Actuators and Eurosensors IX, Digest of Technical Papers, vol. 1*, Stockholm, Sweden,(Jun. 1995),624-627.

Chau, H-L. , "An Ultraminiature Solid-State Pressure Sensor for a Cardiovascular Catheter", *IEEE Transactions on Electron Devices*, vol. 35, No. 12, (Dec. 1988),pp. 2355-2362.

Ji, J., "An Ultraminiature CMOS Pressure Sensor for a Multiplexed Cardiovascular Catheter", *IEEE Transactions on Electron Devices*, vol. 39, No. 10, (Oct. 1992),pp. 2260-2267.

Lau, C., "Rate Adaptive Cardiac Pacing: Single and Dual Chamber", Futura Publishing Company, Inc., Mount Kisco, NY,(1993),pp. 181-194.

Laudon, M. K., "Pulse Output", *Chapter 11 of Design of Pacemakers*, Published by the Institute of Electrical and Electronics Engineers, Inc., New York,(1995),pp. 251-276.

Sakurai, T. , et al., "An Improved Dispenser Cathode", *International Electron Devices Meeting*, Technical Digest,(Dec. 1984),pp. 322-325.

Spiegel, Egbert , "A CMOS Sensor and Signal Conversion Chip for Monitoring Arterial Blood Pressure and Temperature", *IEEE International Solid-State Circuits Conference,*, (Feb. 20, 1992),126-127.

Wagner, B. K., "Electrodes, Leads and Biocompatibility", *Chapter 6 of Design of Cardiac Pacemakers*, Edited by John Webster, published by the Institute of Electrical and Electronics Engineers, Inc., New York,(1995),pp. 132-160.

* cited by examiner

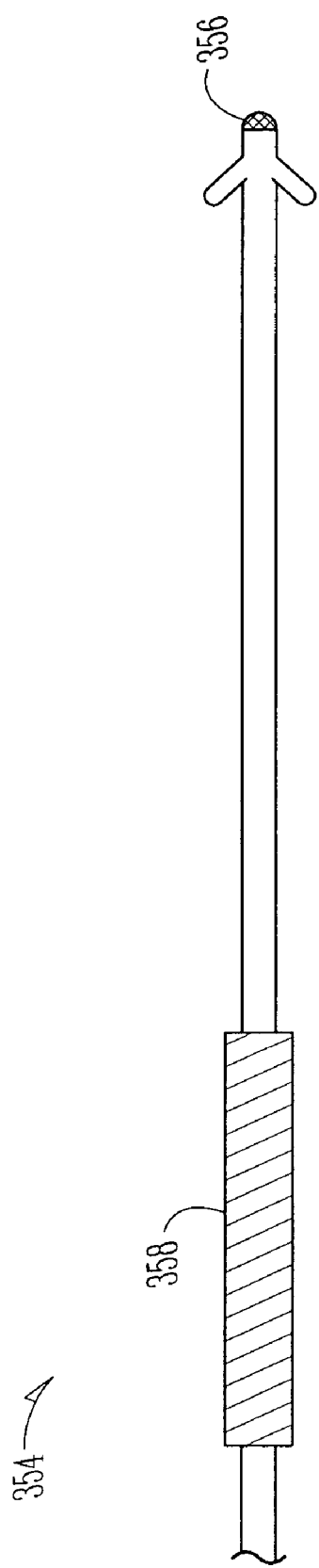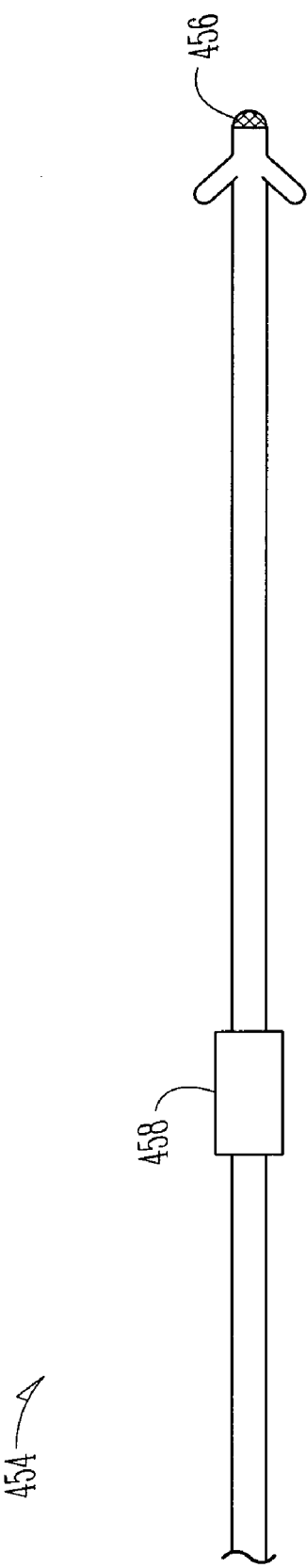

MULTIPLEXED MEDICAL DEVICE LEAD WITH STANDARD HEADER

CROSS-REFERENCE TO RELATED APPLICATION(S)

This application is a division of U.S. patent application Ser. No. 10/008,529, filed on Nov. 7, 2001 now U.S. Pat. No. 6,859,667, the specification of which is incorporated herein by reference.

FIELD OF THE INVENTION

This invention relates generally to the field of medical devices and, more particularly, to cardiac stimulus device leads.

BACKGROUND OF THE INVENTION

A cardiac stimulus device is a medical device, such as an implantable cardiac pacemaker or an implantable cardioverter defibrillator (ICD), for stimulating a heart with an electric signal. Some cardiac stimulus devices are surgically implanted within a patient. An implantable cardiac stimulus device includes a pulse generator and one or more electrical leads with one or more electrodes that conduct signals to and receive signals from the patient's heart. These lead(s) and their electrode(s) are placed in or proximate to the heart such that an electrical signal between electrodes is capable of stimulating the heart. The electrodes may be configured either to produce or pace an electrical cardiac event, or to detect or sense an intrinsic electrical cardiac event. Some medical devices record or otherwise collect these cardiac events. A programming device or programmer communicates with the medical device through a communication link. One example of a communication link is a telemetry link that provides means for commands and data to be non-invasively transmitted and received between the programmer and the device.

The leads of the cardiac stimulus device are connected to the pulse generator using a connector assembly or header. The connector assembly includes a lead connector and a connector cavity for the electrical and mechanical connection of the lead to the pulse generator. An IS-1 header standard has been developed as a design standard for connector assemblies. If cardiac stimulus devices from different manufacturers are designed according to the header standard, a physician has the flexibility to use one manufacturer's leads with another manufacturer's pulse generator.

The electrodes are capable of electrically sensing cardiovascular parameters. For example, the electrodes are capable of sensing intracardiac electrical activity, i.e. intrinsic electrical cardiac events. However, there are difficulties in sensing non-electrical activity or in otherwise providing additional non-electrical sensing capabilities. One of these difficulties involves encapsulation, which is the process that occurs when a foreign body enters the human body. The encapsulation of a sensor is sometimes referred to as biofouling. The immune system of the human body recognizes the foreign body and tries to reject it by building a layer of tissue around the foreign body to protect the rest of the body. Because steroids slow down the encapsulation process, steroid-eluting pacing leads have been developed.

Another difficulty in providing additional sensing capabilities for the lead involves the addition of sensor(s) on the lead. Conventionally, supporting sensor electronics are located in the pulse generator, and electrical conductors are provided between the supporting sensor electronics and the additional sensor(s). These extra conductors require more connections between the lead and the pulse generator, or can, of the cardiac stimulus device, and thus mandate a special header design that violates the header standard. That is, the cardiac stimulus device with the extra sensing capabilities has a special connector assembly and can only be used with special lead(s) that have been designed for the special connector assembly. However, physicians often desire to use one manufacturer's pulse generator with another manufacturer's lead for a number of reasons. These reasons include familiarity, the capabilities of the pulse generator, the capabilities of the leads, cost, quality, and overall flexibility in treating individual patients. As a result, the cardiac stimulus device with the extra sensing capabilities is less marketable because the special header design prevents a physician from mixing and matching leads and pulse generators.

Therefore, there is a need in the art to provide a system and method for providing additional sensing capabilities on a cardiac stimulus device lead without violating header standards.

SUMMARY OF THE INVENTION

The above mentioned problems are addressed by the present subject matter and will be understood by reading and studying the following specification. The present subject matter provides a cardiac stimulus device lead with additional sensing capabilities without violating header standards.

The supporting sensor electronics for the additional sensing capabilities is provided in the lead. A multiplex scheme is used to provide a time slot within a pacing cycle for transmitting data from the additional sensor(s) such that the sensor data is transmitted using the same conductors that are used to deliver pacing pulses to electrodes on the lead. Therefore, according to one embodiment, a pacing pulse is transmitted over the conductors from the pulse generator to the electrodes in a first time slot, sensor data is transmitted over the conductors from the sensor circuitry to the pulse generator in a second time slot, an active discharge pulse is delivered over the conductors from the pulse generator to the electrodes in a third time slot, and intrinsic electrical cardiac signals are transmitted over the conductors from the electrodes to the pulse generator in a fourth time slot. As such, the additional sensing capabilities are provided without violating the header standards.

One aspect of the present subject matter is a cardiac stimulus device lead. According to one embodiment, the lead includes a first conductor and a second conductor for transmitting an electrical pulse from a pulse generator. The lead further includes a multiplexer switch, a first electrode, a second electrode, a sensing circuit and a controller. The first conductor is connected to the multiplexer switch. A first terminal of the multiplexer switch is connected to the first electrode and a second terminal of the multiplexer switch is connected to the sensing circuit. The second conductor is connected to the second electrode. The controller is connected to the multiplexer switch, and is adapted to selectively connect the first conductor to one of the first electrode and the sensing circuit.

According to one embodiment, the lead includes a first conductor and a second conductor for transmitting an electrical pulse from a pulse generator. The electrical pulse has a cycle that includes a pacing pulse. The lead further includes a first electrode and a sensing circuit. The first conductor is selectively coupled either to the first electrode or to an output of the sensing circuit. The lead further includes a controller coupled to the sensing circuit. The controller is adapted for providing a multiplex scheme to transmit sensor data from the sensing circuit on the first conductor after the pacing pulse.

According to one embodiment, the lead includes a first conductor and a second conductor for transmitting an electrical pulse from a pulse generator. A capacitor is selectively coupled between the first conductor and the second conductor and is adapted for storing a charge from the electrical pulse. A first electrode is selectively coupled to the first conductor. A power input of a sensing circuit (SC) is selectively coupled to the capacitor for being powered by the charge stored thereon. An output of the sensing circuit is selectively coupled to the first conductor. A controller is coupled to the capacitor to be powered by the charge stored thereon, and is further coupled to the control input of the sensing circuit. The controller includes SC control circuitry, capacitor coupling control circuitry, and SC output control circuitry. The SC control circuitry controls the sensing circuit. The capacitor coupling control circuitry selectively couples the capacitor between the first conductor and the second conductor. The SC output control circuitry selectively couples the first conductor to either the output of the sensing circuit or to the first electrode.

Another aspect of the present subject matter is a method for generating pacing pulses and outputting additional sensor data on shared electrodes. According to one embodiment of this method, a pacing pulse is generated by a pulse generator and transmitted on lead conductors. Sensor data is processed and output by a sensing circuit on the lead conductors. An active discharge pulse is initiated by the pulse generator, and preparations are made for a subsequent pacing pulse. According to one embodiment, the sensor data is output in a predetermined time slot with respect to the pacing pulse.

These and other aspects, embodiments, advantages, and features will become apparent from the following description of the invention and the referenced drawings.

BRIEF DESCRIPTION OF THE DRAWINGS

FIG. 3 illustrates a first lead example.

FIG. 4 illustrates a second lead example.

DETAILED DESCRIPTION OF THE INVENTION

Figure 1:
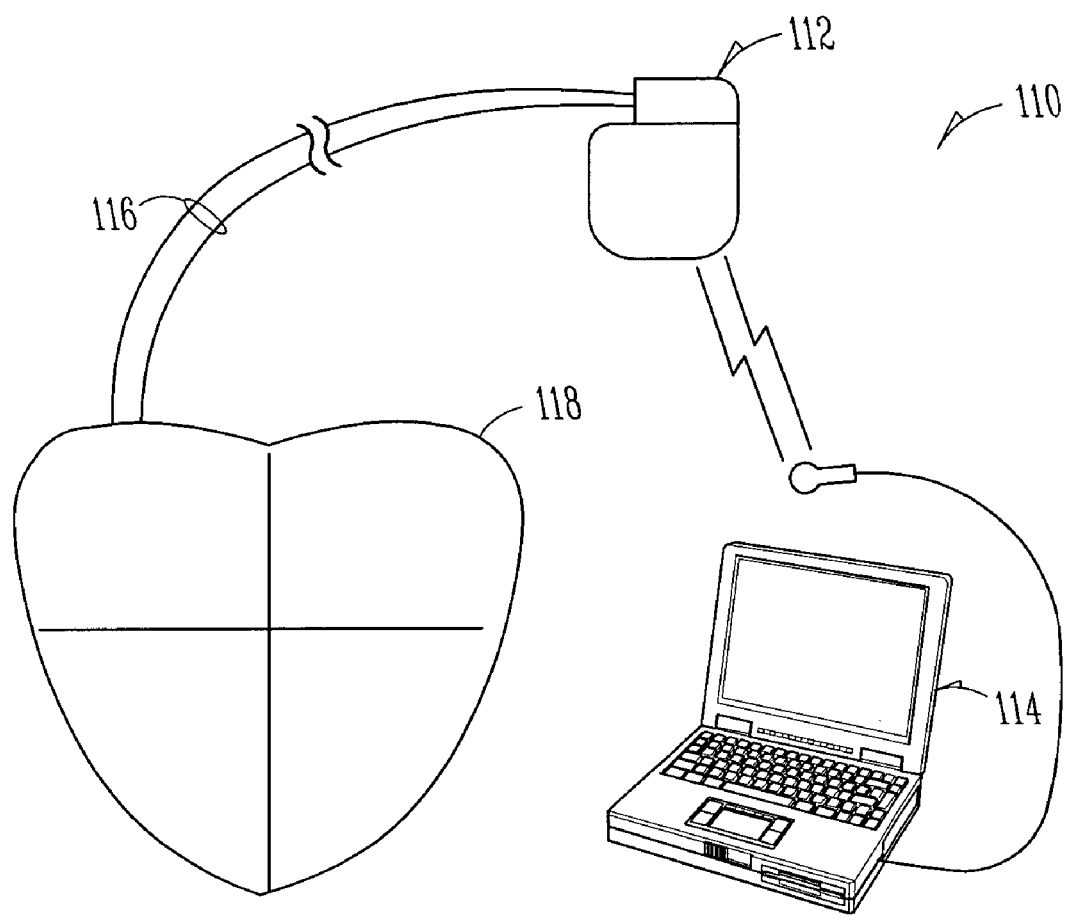
FIG. 1 is an illustration of a cardiac rhythm management system.

The following detailed description of the invention refers to the accompanying drawings which show, by way of illustration, specific aspects and embodiments in which the invention may be practiced. In the drawings, like numerals describe substantially similar components throughout the several views. These embodiments are described in sufficient detail to enable those skilled in the art to practice the invention. Other embodiments may be utilized and structural, logical, and electrical changes may be made without departing from the scope of the present invention. The following detailed description is, therefore, not to be taken in a limiting sense, and the scope of the present invention is defined only by the appended claims, along with the full scope of equivalents to which such claims are entitled.

The present subject matter provides a cardiac stimulus device lead with additional sensing capabilities without violating header standards. The supporting sensor electronics for the additional sensing capabilities is provided in the lead. A multiplex scheme is used to provide a time slot within a pacing cycle for transmitting data from the additional sensor(s) such that the sensor data is transmitted using the same conductors that are used to deliver pacing pulses to electrodes on the lead. As such, the additional sensing capabilities are provided without violating the header standards.

FIG. 1 is an illustration of a cardiac rhythm management system. The system 110 generally comprises a cardiac stimulus device 112 and a programmer 114 that is capable of communicating with the cardiac stimulus device 112. According to one embodiment, the cardiac stimulus device 112 is a pacemaker. According to another embodiment, the cardiac stimulus device 112 is an ICD. One of ordinary skill in the art will understand that the term cardiac stimulus device is not limited to those devices characterized as pacemakers and ICDs. The cardiac stimulus device 112 has an electrode system 116 that includes at least one lead and at least one electrode for each lead. FIG. 1 shows an example in which there are two leads. The leads are inserted into or proximate to a patient's heart 118. The electrode system 116 transmits electrical signals or pulses to stimulate the heart 118 and receives or senses electrical signals from the heart 118. The lead(s) and electrode(s) of the electrode system 116 are arranged, programmed and/or otherwise configured to provide the cardiac stimulus device 112 with a desired configuration in an attempt to optimize the operation of the cardiac stimulus device 112 for a particular patient.

Figure 2:
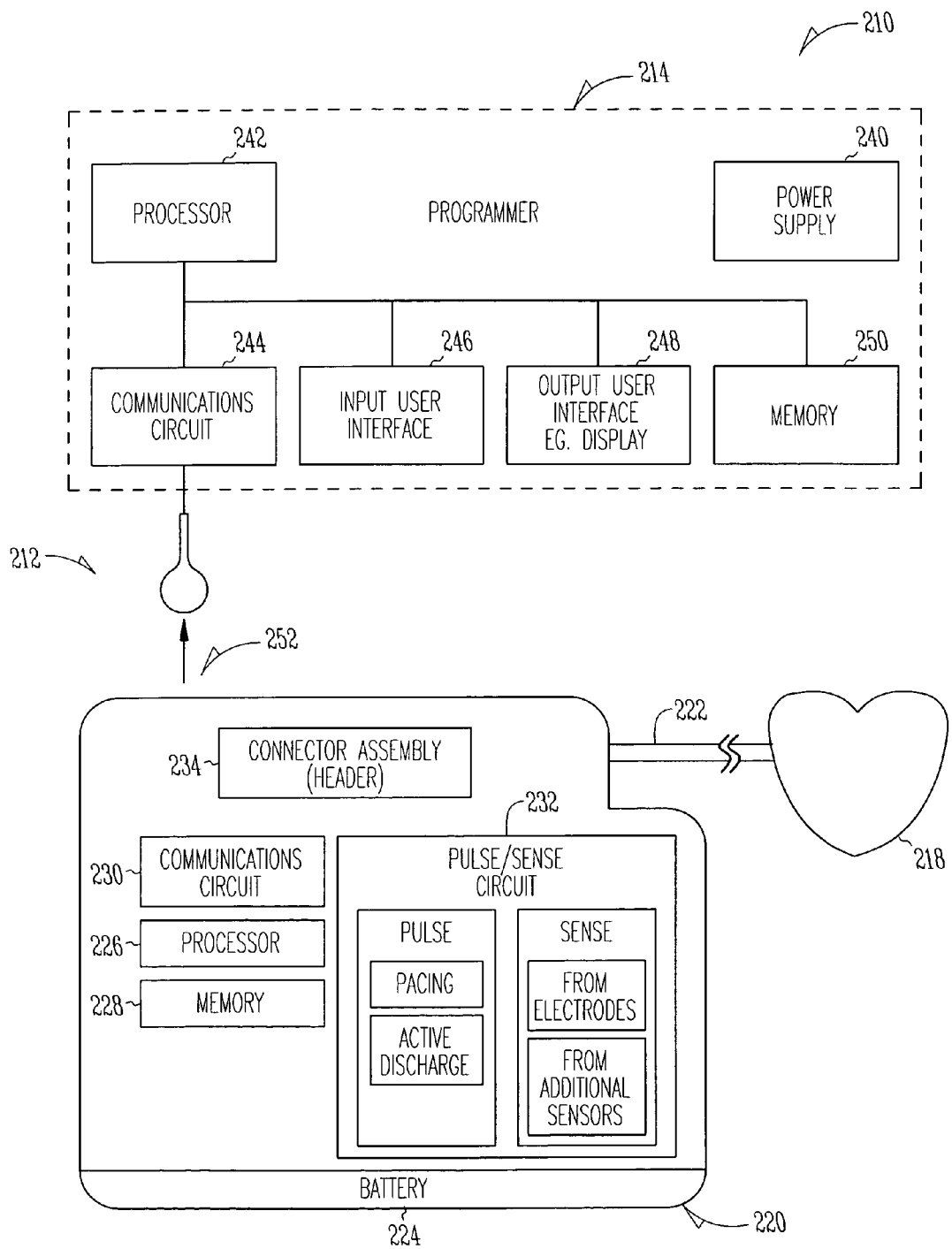
FIG. 2 is another illustration of the cardiac rhythm management system.

FIG. 2 is another illustration of the cardiac rhythm management system. The system 210 includes a cardiac stimulus device 212 and a programmer 214. According to one embodiment, the cardiac stimulus device 212 is a programmable microprocessor-based system that includes a pulse generator or can 220, and attachable electrode system leads 222. According to one embodiment, the pulse generator 220 includes a power source such as a battery 224, a processor 226, a memory 228, a communications circuit 230, and a pulse/sense circuit 232. The processor 226, memory 228, communication circuit 230 and pulse/sense circuit 232 are in operable communication with each other. The processor 226 and memory 228 are used to control the process steps conducted by the cardiac stimulus device 212. The pulse/sense circuit 232 generates electrical pulses and transmits the pulses through the electrode system leads 222 to the heart 218. The pulse/sense circuit 232 also receives sensed intrinsic electrical signals through the electrode system leads 222 from the heart 218.

The cardiac stimulus device 212 also includes a connector assembly 234 or header that comprises an interface for coupling the electrode system leads 222 to the pulse generator 220. According to one embodiment, the connector assembly 234 includes a lead connector and a connector cavity for the electrical and mechanical connection of the lead(s) 222 to the pulse generator 220. According to one embodiment, the connector assembly 234 is designed according to a header standard. Pulse generators 220 and electrode system leads 222 of one manufacturer are interchangeable with those from another manufacturer if both manufacturers follow the header standard in their design.

One aspect of the present subject matter, which will be discussed in more detail below, provides additional sensing capabilities on the leads 222. According to this aspect, the pulse/sense circuit 232 includes circuitry for processing the additional sensor information. According to one embodiment, a multiplexing scheme is used. According to one embodiment of the multiplexing scheme, several events or electrical signals are transmitted on shared conductors. According to this embodiment, these events include transmitting pacing pulses from the pulse generator to the electrodes on the leads, transmitting additional sensor information from additional sensor(s) on the lead to the pulse generator, transmitting an active discharge pulse from the pulse generator to the electrodes, and transmitting intrinsic electrical signals from the electrodes to the pulse generator. According to one embodiment, the multiplexing scheme is a time division multiplexing scheme wherein each event has a time slot on which the transmission can occur on the shared conductors.

According to one embodiment, the programmer 214, or processing device, includes a power supply 240, a processor 242, a communications circuit 244, an input user interface 246, an output user interface 248, and a memory 250 that are in operable communication with each other. The programmer 214 is capable of communicating with the cardiac stimulus device 212 through a communication channel 252. In one embodiment, the communication circuits 244 and 230 provide a radio frequency telemetry channel between the programmer 214 and the cardiac stimulus device 212. In another embodiment, the cardiac stimulus device 212 and programmer 214 communicate with each other using inductive coils. The input user interface 246 includes, but is not limited to, a keyboard, a mouse, a light pen and a touch screen. The output user interface 248 includes, but is not limited to, printers and displays. According to one embodiment, the programmer 214 is capable of programming the cardiac stimulus device 212, including the configuration of the electrode system, and is capable of collecting data from the sensors.

Figure 5:
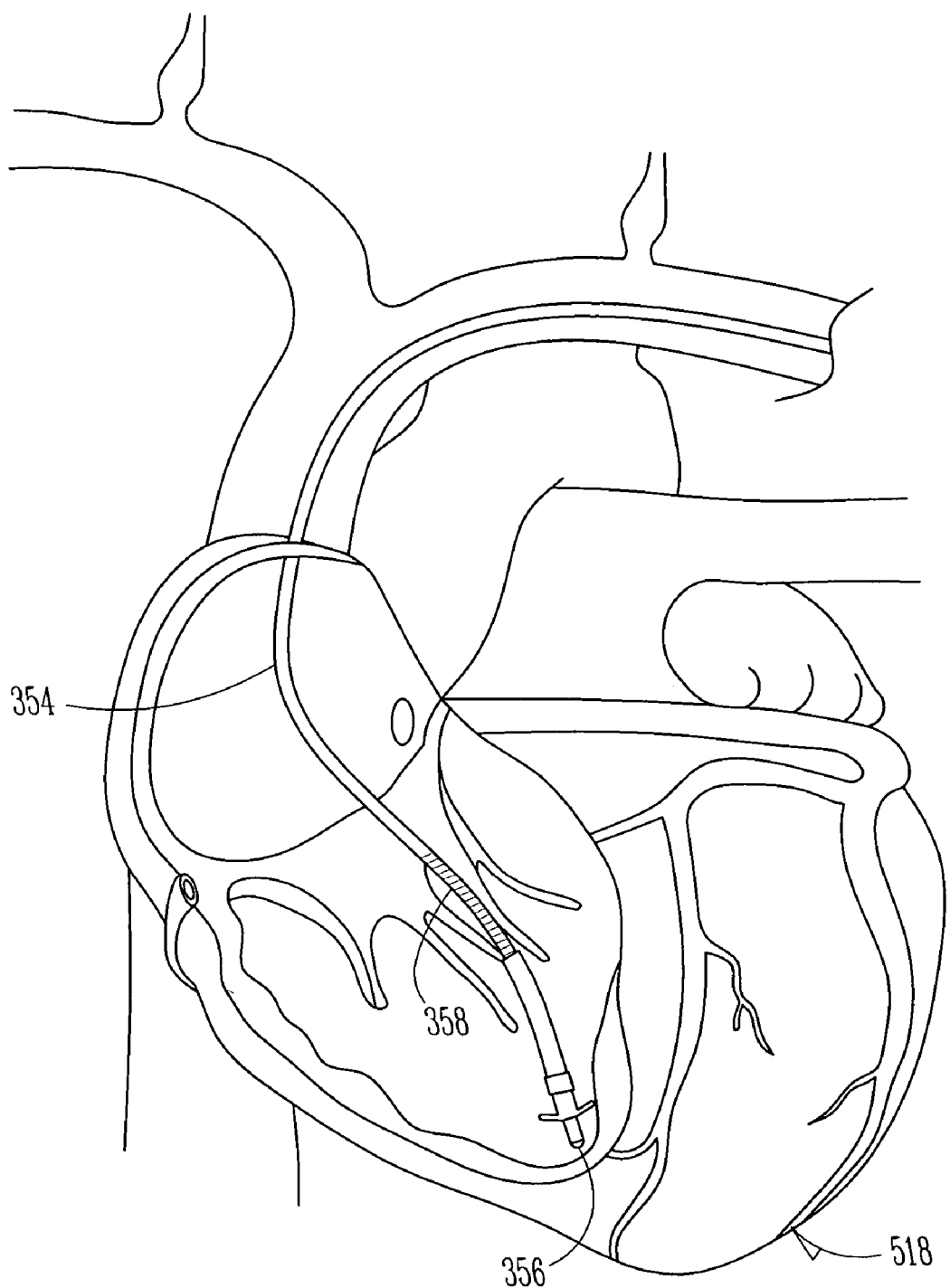
FIG. 5 illustrates one arrangement of the lead shown in FIG. 3.
Figure 6:
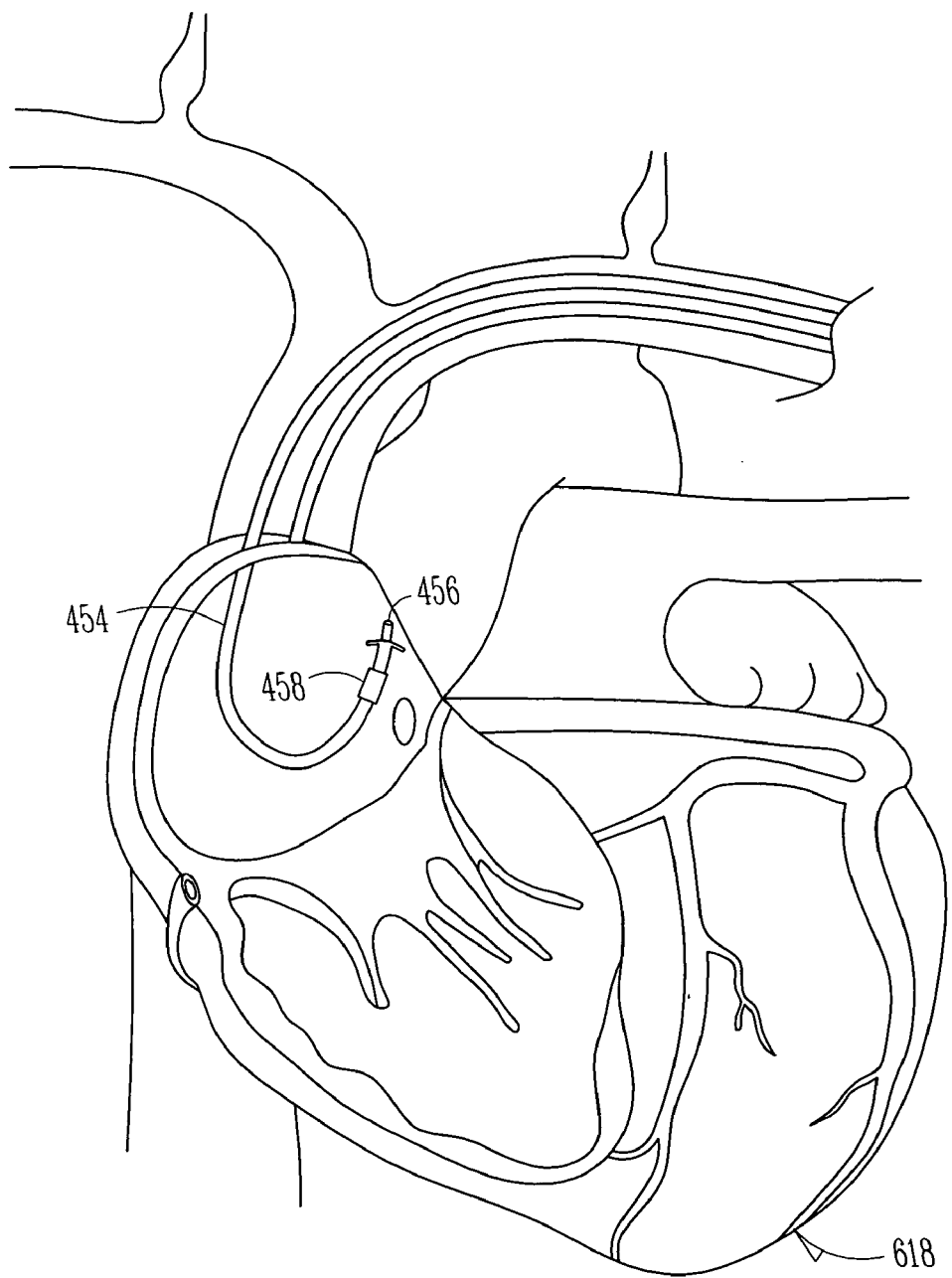
FIG. 6 illustrates one arrangement of the lead shown in FIG. 4.

FIG. 3 illustrates a first lead 354, and FIG. 4 illustrates a second lead 454. Although not drawn to scale, these two illustrations are provided as examples of leads. In no way should the inclusion of this example be interpreted to limit the invention to a particular type of lead. The first lead 354 shown in FIG. 3 includes a tip electrode 356 and a first coil electrode 358. The first lead 354 may be used, for example, in an implantable cardioverter defibrillator. The second lead 454 shown in FIG. 4 includes a tip electrode 456 and a first ring electrode 458. The second lead 454 may be used, for example, in an implantable pacemaker. FIG. 5 illustrates one arrangement of the first lead 354 in a heart 518 and FIG. 6 illustrates one arrangement of the second lead 454 in a heart 618. These arrangements are provided as examples only, and should not be interpreted to limit the invention to a particular lead arrangement or electrode configuration. For example, a pulse may be provided between two or more electrodes on the same lead, between two or more electrodes on different leads, and between a conductive surface on the pulse generator and one or more electrodes on one or more leads. Additionally, one of ordinary skill in the art will understand that the leads and electrodes are capable of being placed in a number of areas or locations, including those areas that are commonly used at the present time.

The electrode system is capable of sensing intracardiac electrical activity. Since the leads are already in place for the purpose of stimulating a heart, it is desirable to provide the lead with additional sensing capabilities such as, but not limited to, biochemical sensing capabilities. The present subject matter addresses the previously-described difficulties involved with including additional sensors on the lead and sensing more than intracardiac electrical activity.

Sensors and supporting electronics are capable of being fabricated using micro-electromechanical systems (MEMS) or using other semiconductor technology. A MEMS device contains micro-circuitry on a tiny silicon chip into which some mechanical device such as a sensor has been manufactured. These chips can be built in large quantities at low cost, making the MEMS device cost-effective. MEMS devices have been used in catheter-based systems to measure chronic intracardiac pressure and temperature.

According to one embodiment, additional sensor(s) and supporting electronics are incorporated into a cardiac stimulus device lead. According to one embodiment, a MEMS device is incorporated into a cardiac stimulus device lead, such as a standard pacing or defibrillation lead, to provide additional sensor(s) and supporting electronics. Including a MEMS device on a standard cardiac stimulus device lead combines the traditional electrical pacing and sensing functions of a cardiac stimulus device lead with additional sensing capabilities. The sensor(s) associated with the MEMS device(s) is capable of being positioned anywhere along the lead as desired for the application. As will be discussed in more detail below, a multiplexing scheme is used to incorporate the MEMS device on a standard lead without requiring any additional connections between the lead and the pulse generator. As a result, a standard cardiac stimulus device is provided with extra sensing capability without deviating from the IS header standard.

Figure 7:
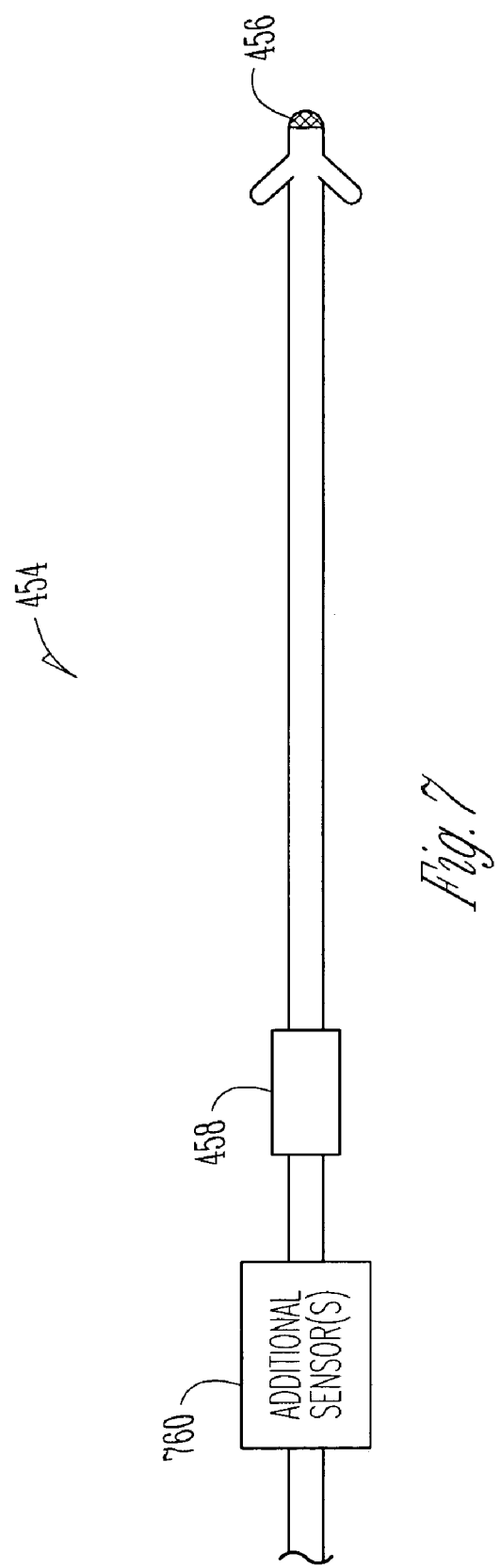
FIG. 7 illustrates one embodiment wherein additional sensor(s) are added to a standard lead.
Figure 8:
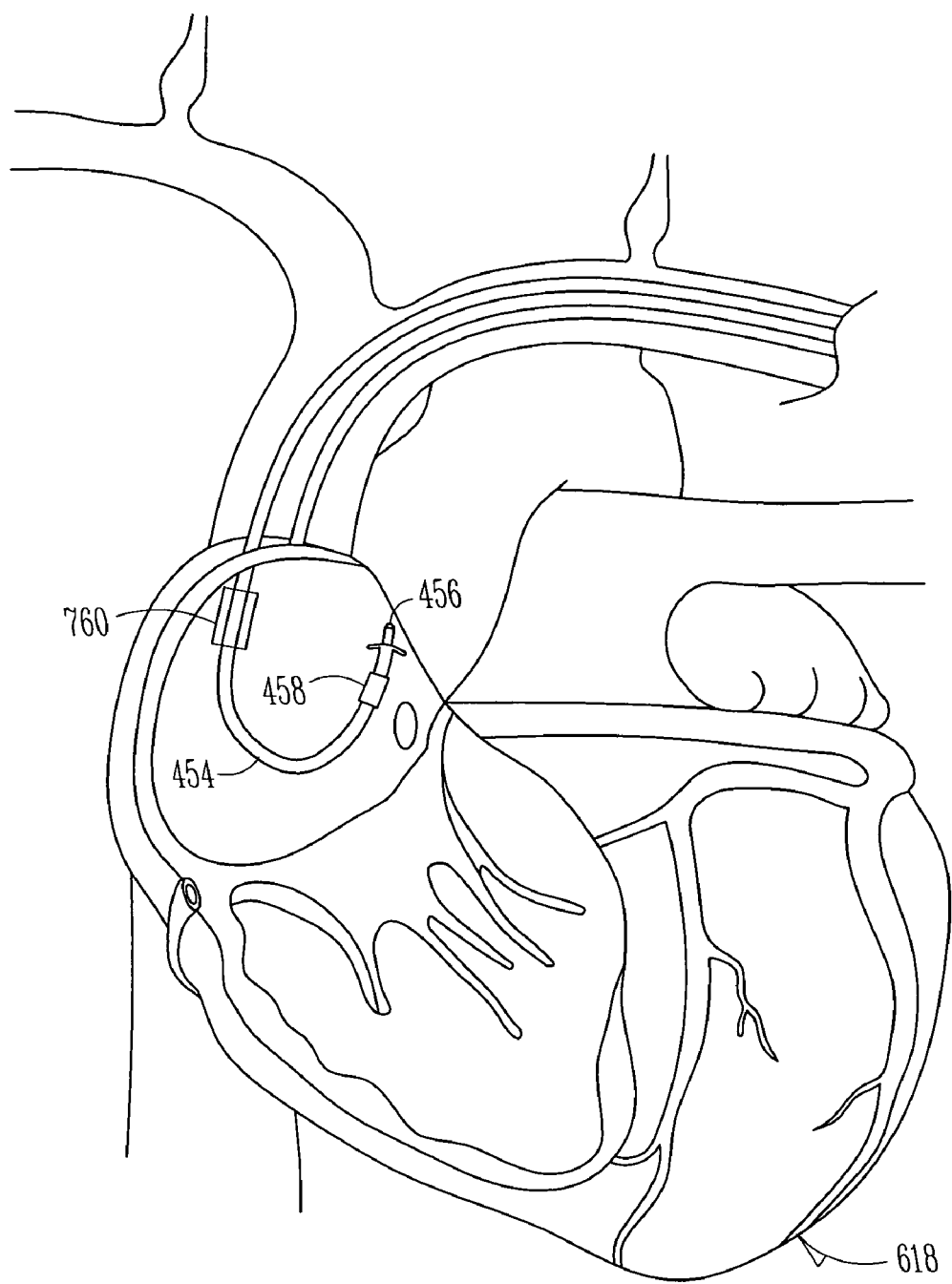
FIG. 8 illustrates one arrangement of the lead shown in FIG. 7.

FIG. 7 illustrates one embodiment wherein additional sensor(s) are added to a standard lead. According to the illustrated embodiment, sensor(s) 760 are added to the tip electrode 456 and the ring electrode 458 for the second lead 454 that was previously shown in FIG. 4. According to one embodiment, the additional sensor(s) 760 include a MEMS device. FIG. 8 illustrates one arrangement of the lead shown in FIG. 7. The illustrations provided in FIGS. 7 and 8 should not be interpreted to limit the present invention to a particular type of lead or to a particular lead arrangement or electrode configuration. According to one embodiment, the additional sensor(s) are biochemical sensors. In other embodiments, the additional sensor(s) sense oxygen, carbon dioxide, catecholamines, pressure and/or temperature. However, the present invention is not so limited.

Figure 9:
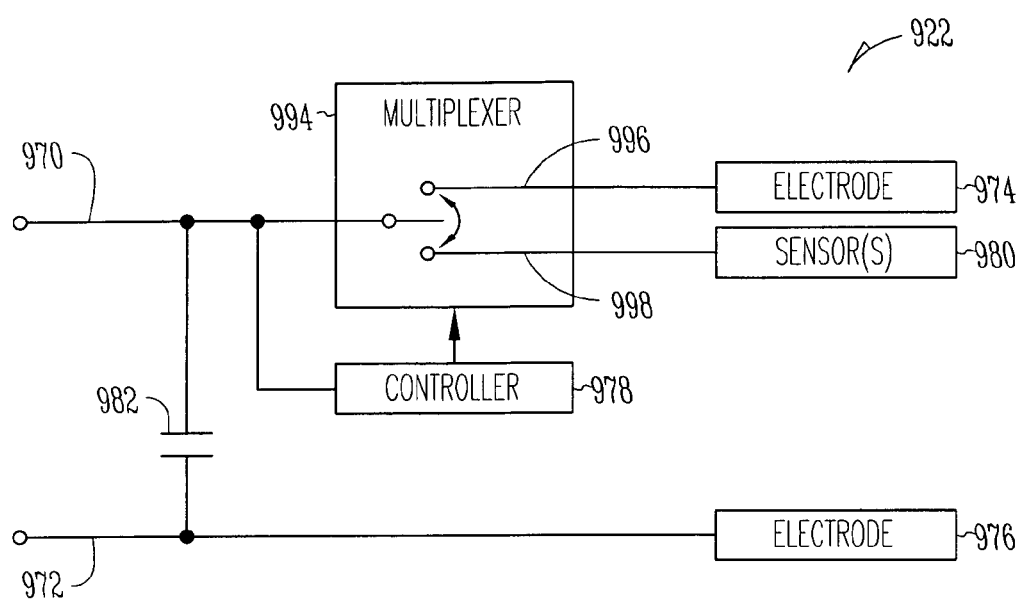
FIG. 9 provides a schematic illustration of one embodiment of the cardiac stimulus device according the present subject matter.

FIG. 9 provides a schematic illustration of one embodiment of the cardiac stimulus device according the present subject matter. According to this embodiment, the lead 922 includes a first conductor 970 and a second conductor 972 for connecting to electrodes 974 and 976. It is noted that the conductors 970 and 972 are connected to different types and arrangements of electrode(s) as may be appropriate to provide the desired therapy to a patient. For example, in a unipolar pacing arrangement, one of the conductors is coupled to a conductive surface of a pulse generator. The lead 922 includes a capacitor 982, a multiplexer 994 illustrated as a multiplexer switch, a sensing circuit or sensor(s) 980, and a controller 978. The first conductor 970 is connected to the multiplexer switch 994. A first terminal 996 of the multiplexer switch 994 is connected to the first electrode 974 and a second terminal 998 of the multiplexer switch 994 is connected to the sensor(s) 980. The second conductor 972 is connected to the second electrode 976. The controller 978 is connected to the multiplexer switch 994, and is adapted to selectively connect the first conductor 970 to one of the first electrode 974 and the sensor(s) 980. The controller 978 is further connected to the first conductor 970. The controller 978 is adapted to sense a pacing pulse on the first conductor 970, and is powered by the charge stored on the capacitor 982 between pacing pulses. The controller 978 provides a control signal to couple the first conductor 970 to the sensor(s) after the pacing pulse. In one embodiment that is described in more detail below, the controller 978 is adapted to sense an electrical pulse, such as a subthreshold pulse, to trigger a control signal to couple the first conductor 970 to the sensor(s).

Figure 10:
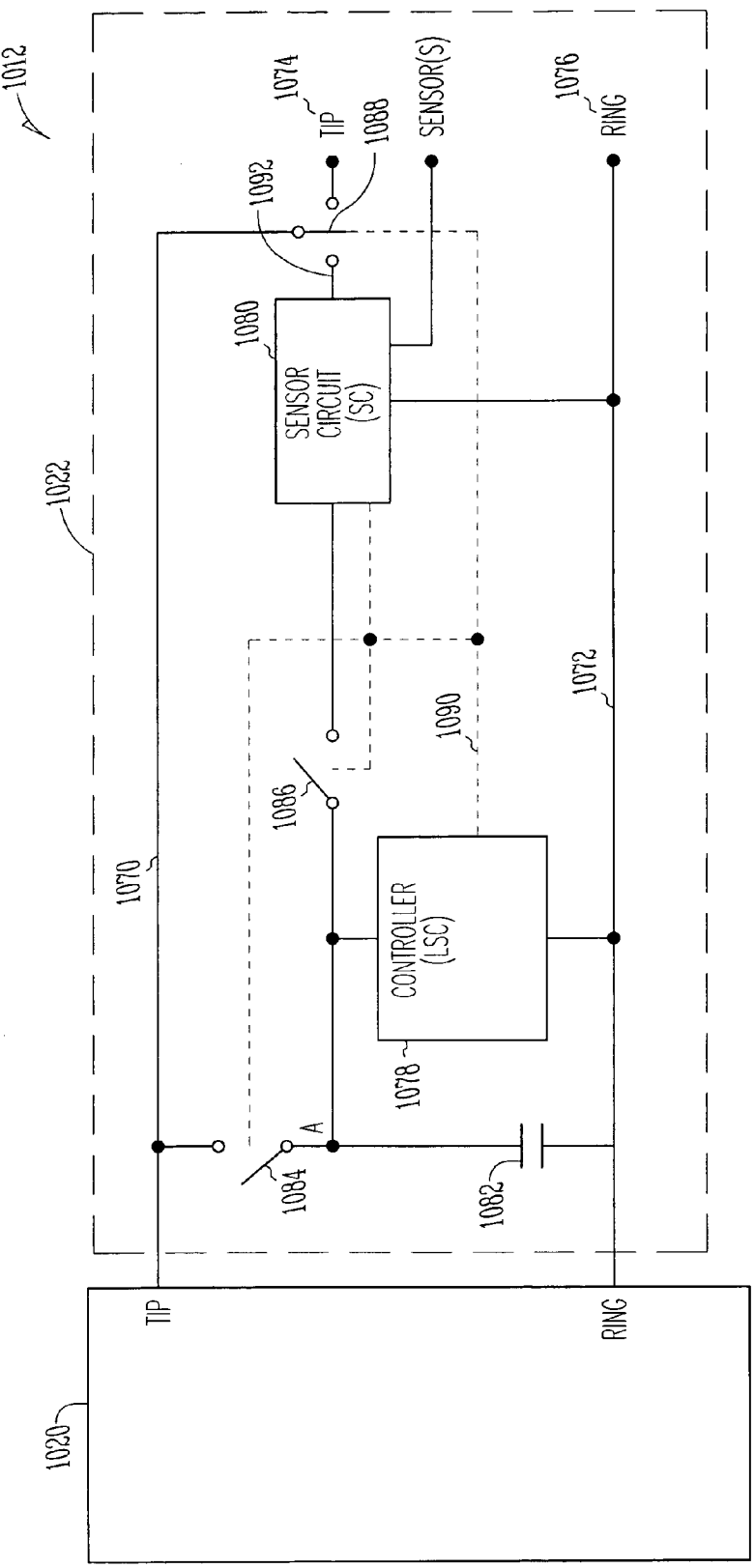
FIG. 10 provides a schematic illustration of one embodiment of the cardiac stimulus device according the present subject matter.

FIG. 10 provides a schematic illustration of one embodiment of the cardiac stimulus device according the present subject matter. The cardiac stimulus device 1012 includes a pulse generator or can 1020, and at least one attachable lead 1022. The lead 1022 is attached to the pulse generator 1020 according to a standard header. According to this embodiment, the lead 1022 includes a first conductor 1070 and a second conductor 1072 for connecting to a tip and ring electrodes 1074 and 1076. It is noted that the conductors are connected to different types and arrangements of electrode(s) as may be appropriate to provide the desired therapy to a patient. For example, in a unipolar pacing arrangement, one of the conductors is coupled to a conductive surface of the pulse generator 1020.

The lead 1022 also includes a controller 1078 or lead sensor controller (LSC), and a sensor circuit (SC) 1080. According to one embodiment, the sensor circuit 1080 is a MEMS device. According to one embodiment, the controller 1078 is adapted for providing a multiplex scheme to transmit sensor data from the sensing circuit on at least one of the conductors after the pacing pulse. According to one embodiment, the controller 1078 transmits sensor data after sensing a pacing pulse. In one embodiment, the controller 1078 transmits sensor data after detecting another electrical signal, such as a subthreshold pulse. The lead 1022 also includes a capacitor 1082, a first switch 1084, a second switch 1086, and a third or multiplexer switch 1088. The sensor circuit 1080 and each of the switches 1084, 1086 and 1088 are controlled by the controller 1078, as illustrated by the dotted line 1090.

The first switch 1084 selectively couples the capacitor 1082 between the first and second conductors 1070 and 1072. A charge is stored on the capacitor 1082 when the first switch 1084 is closed and when a pulse is transmitted on the first and second conductors 1070 and 1072. That is, the capacitor 1082 bleeds energy from the pacing pulse. A Node A is formed between the first switch 1084 and the capacitor 1082. The controller 1078 is coupled to Node A and across the capacitor 1082 such that it is powered by the charge stored in the capacitor 1082.

The second switch 1086 selectively couples the sensor circuit 1080 to the capacitor 1082 at Node A. The sensor circuit 1080 is powered by the charge stored in the capacitor when the second switch 1086 is closed. The second switch 1086 minimizes the amount of power required by the sensor circuit 1080.

The third switch 1088 selectively couples the first conductor 1070 to either the tip electrode 1074 or to an output 1092 of the sensor circuit 1080. During at least one time slot of the multiplex scheme, the third switch 1088 is coupled to the tip electrode 1074. In this position, the pulse generator 1020 transmits a pacing pulse. Additionally, according to one embodiment, an active discharge pulse is transmitted, and the intrinsic cardiac electrical signal is sensed when the third switch 1088 is coupled to the electrode 1074. During at least one other time slot of the multiplex scheme, the third switch 1088 is coupled to the output 1092 of the sensor circuit 1080. In this position, data from the additional sensor(s) is output from the sensor circuit 1080 to the pulse generator 1020.

Figure 11:
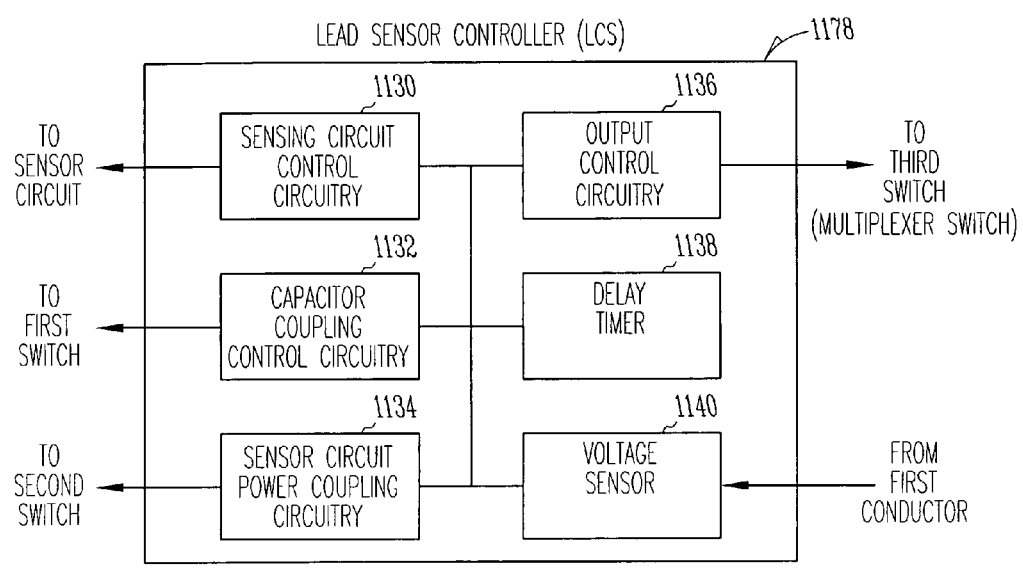
FIG. 11 illustrates one embodiment of a lead sensor controller.

FIG. 11 illustrates one embodiment of a controller, or lead sensor controller. According to this embodiment, the controller 1178 includes sensing circuit control circuitry 1130, capacitor coupling control circuitry 1132, sensor circuit power coupling circuitry 1134, and output control circuitry 1136. Referring also to FIG. 10, the sensing circuit control circuitry 1130 provides a control signal output to the sensing circuit 1080, the capacitor coupling control circuitry 1132 provides an output to the first switch 1084, the sensor circuit power coupling circuitry 1134 provides a control signal output to the second switch 1086, and the output control circuitry 1136 provides a control signal output to the third switch 1088. According to one embodiment, the lead sensor controller 1178 also includes a timer 1138, or delay timer, used to control the timing of the control signal outputs. By controlling the timing of the control signal outputs, the timer 1138 assigns a time slot in which the sensor circuit 1080 transmits sensor data on the shared conductors 1070 and 1072, and also performs activities to cooperate with those activities performed by the pulse generator 1020. A voltage sensor 1140 is adapted to sense a pacing pulse on the first conductor 1070 with respect to a known or common reference voltage. The detected pacing pulse triggers the timer to control the timing of the control signal outputs.

FIGS. 12A through 12E illustrate the behavior of one embodiment of a cardiac stimulus device lead 1222 according to the present subject matter. In an initial condition illustrated in FIG. 12A, the first switch 1284 is closed, the second switch 1286 is open, and the third switch 1288 is in contact with the tip electrode 1274. A pacing pulse is generated from the can or pulse generator 1220. The pacing pulse charges the capacitor 1282 as it bleeds energy from the pacing pulse. The charge stored on the capacitor is used to power the sensor and supporting circuitry for a finite period of time. The lead sensor controller (LSC) 1278 senses the pacing pulse and waits a predetermined amount of time (such as several milliseconds) to allow the pacing pulse to be delivered.

Figure 12A:
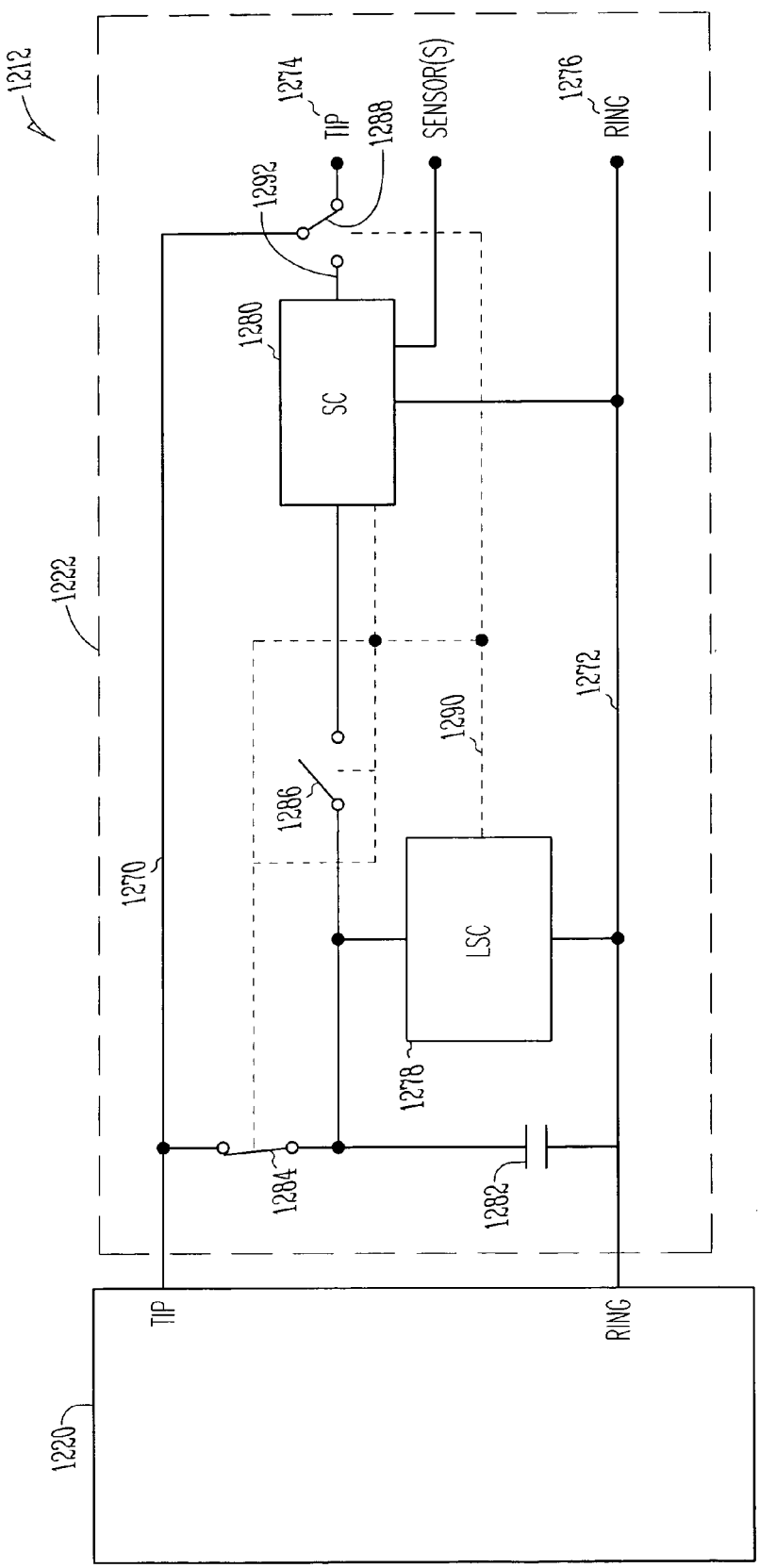
FIGS. 12A through 12E illustrate the behavior of one embodiment of a cardiac stimulus device lead according to the present subject matter.
Figure 12B:
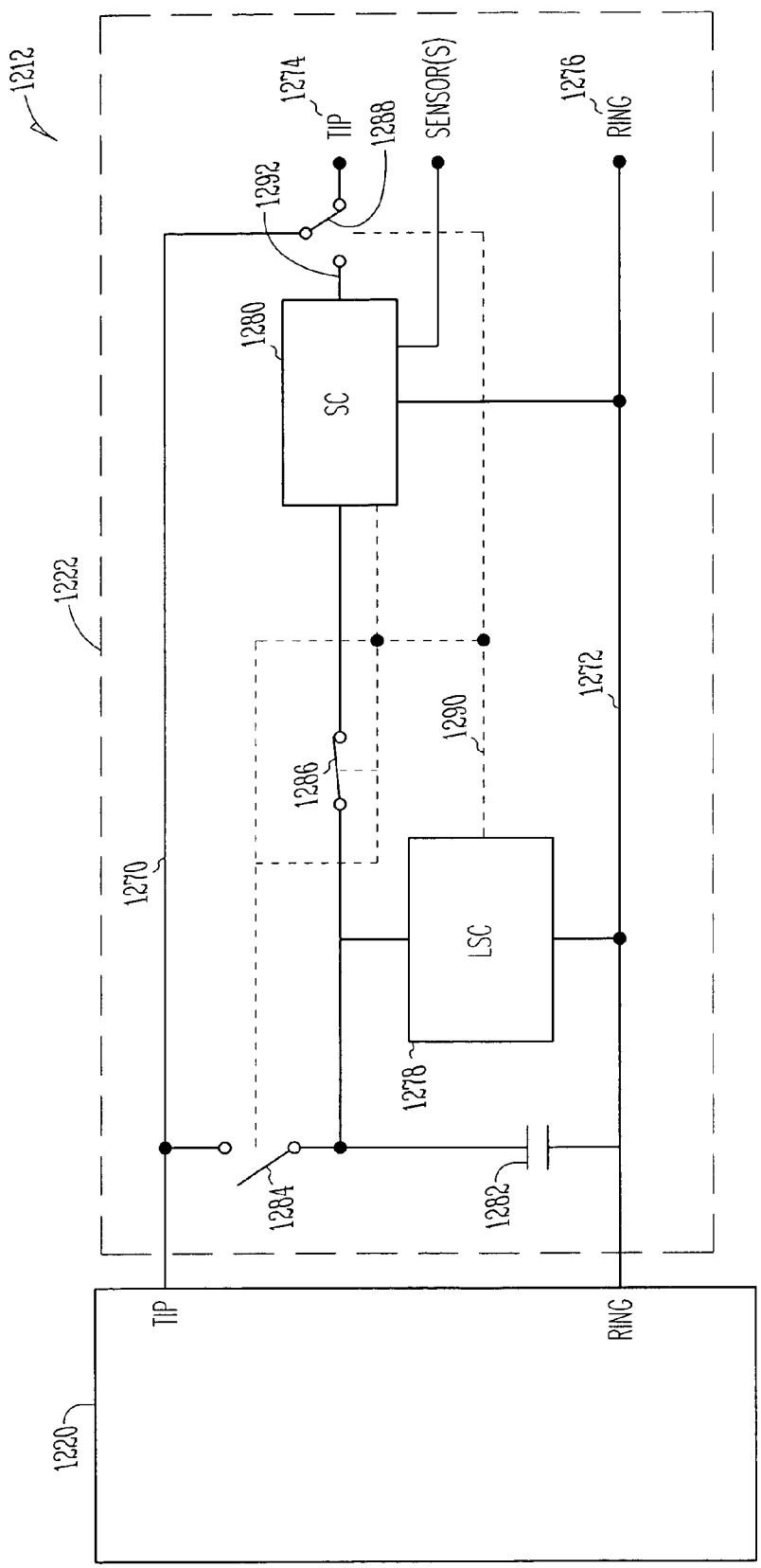
Figure 13:
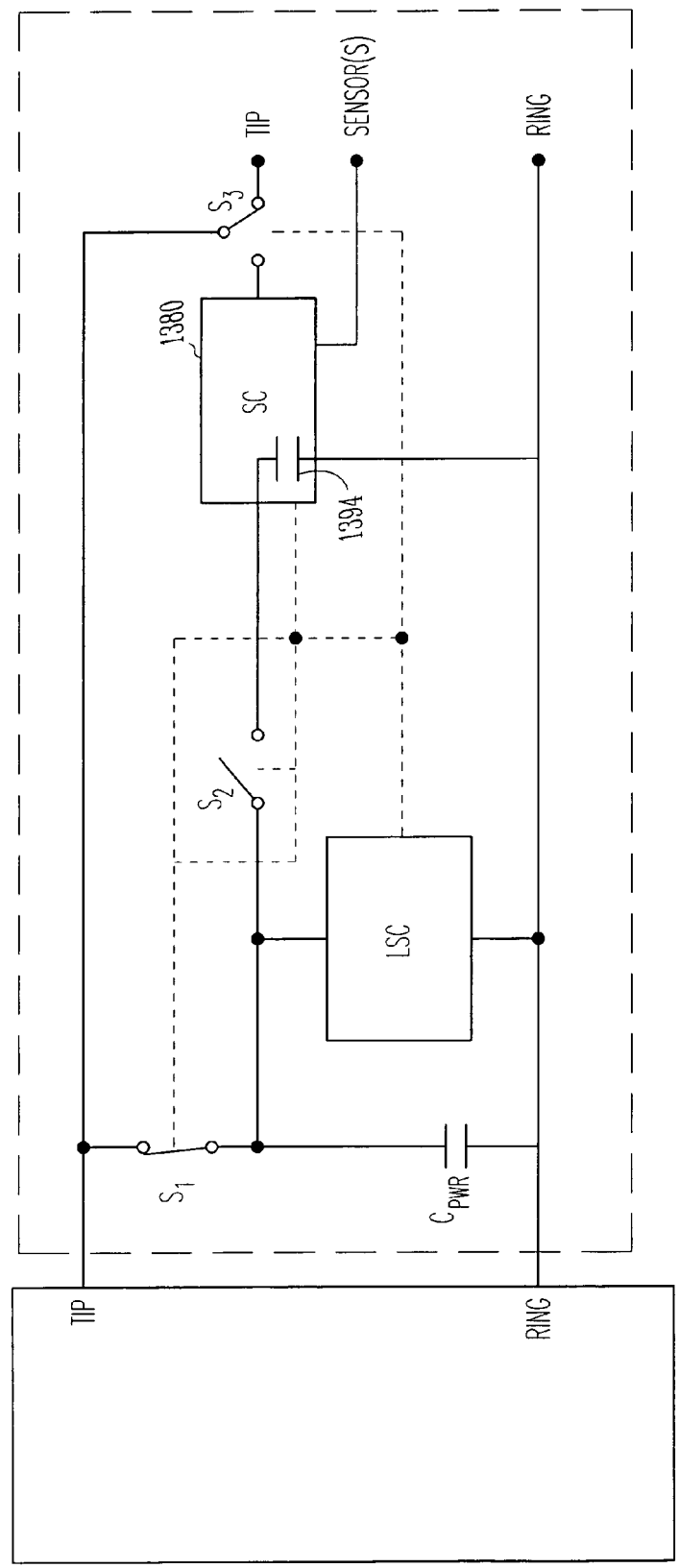
FIG. 13 illustrates another embodiment of a cardiac stimulus device lead.

Referring to FIG. 12B, after the pacing pulse and before a subsequent active discharge pulse, the controller 1278 opens the first switch 1284 and closes the second switch 1286 to provide power to the sensing circuit 1280 from the charge stored on the capacitor 1282. According to one embodiment, the sensing circuit 1280 processes the sensor data for output after the second switch 1286 is closed. According to one embodiment, as illustrated in FIG. 13, the sensing circuit 1380 may also contain a small power supply capacitor 1394 to continuously provide power to the sensing circuit 1380 and allow sensing between pacing pulses; i.e., continuous sensing. In this embodiment, the closing of the switch periodically re-charges the power supply capacitor 1394 for the sensing circuit 1380.

Figure 12C:
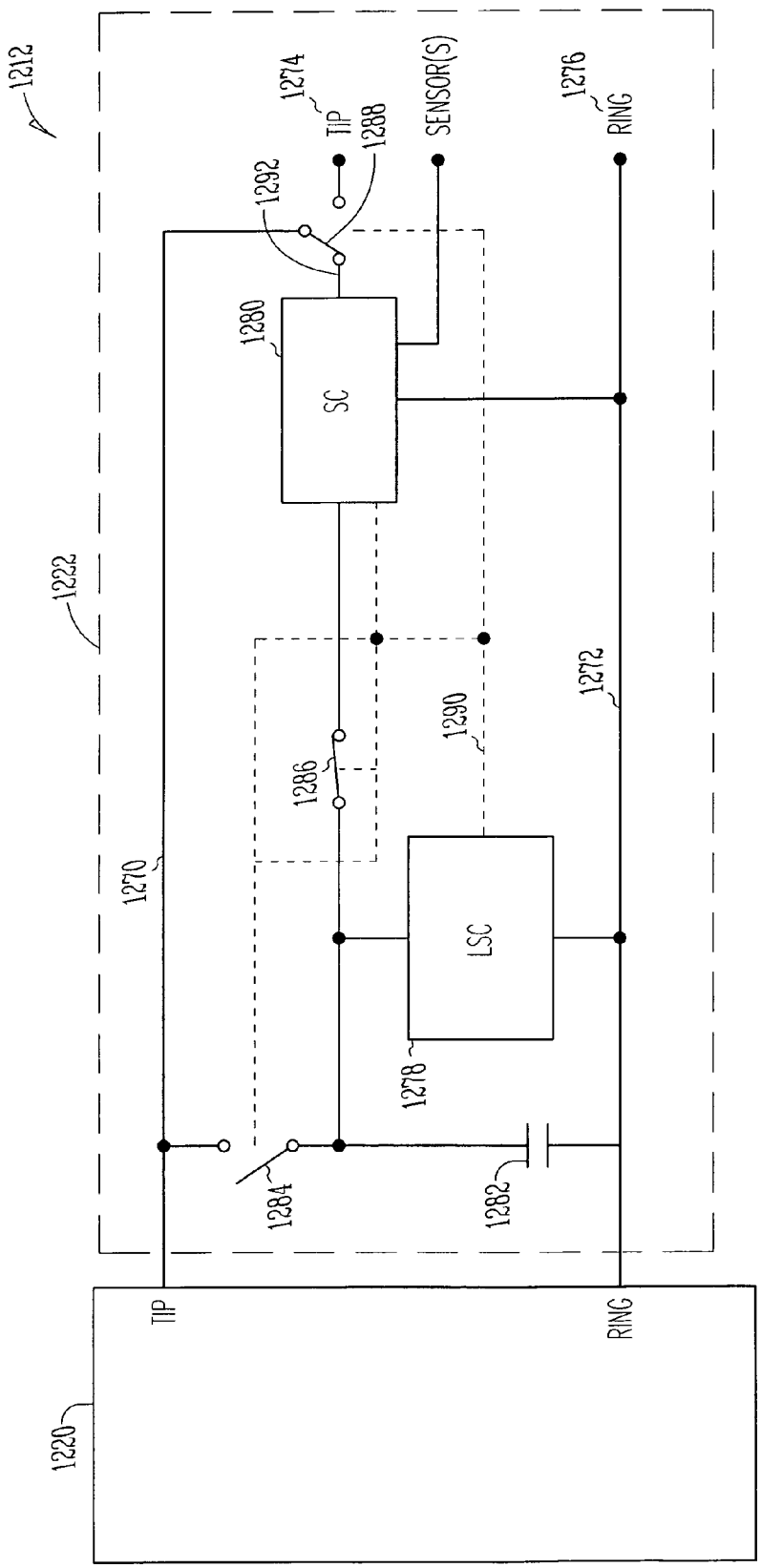

Referring to FIG. 12C, after a predetermined delay, the controller 1278 switches the third switch 1288 from the tip electrode 1274 to the sensor circuit output 1292. The sensing circuit 1280 then outputs the sensor data to the pulse generator 1220 through the first conductor 1270 with respect to a common reference voltage. According to various embodiments, the sensor data includes pre-pace sensor values, post-pace sensor values, or both pre-pace and post-pace sensor values. Knowing the time delay between the delivery of the pacing pulse and the closing of the third switch 1288, the pulse generator 1220 then switches the first and second conductors 1270 and 1272 from its pacing output circuitry to its sensor input circuitry.

Figure 12D:
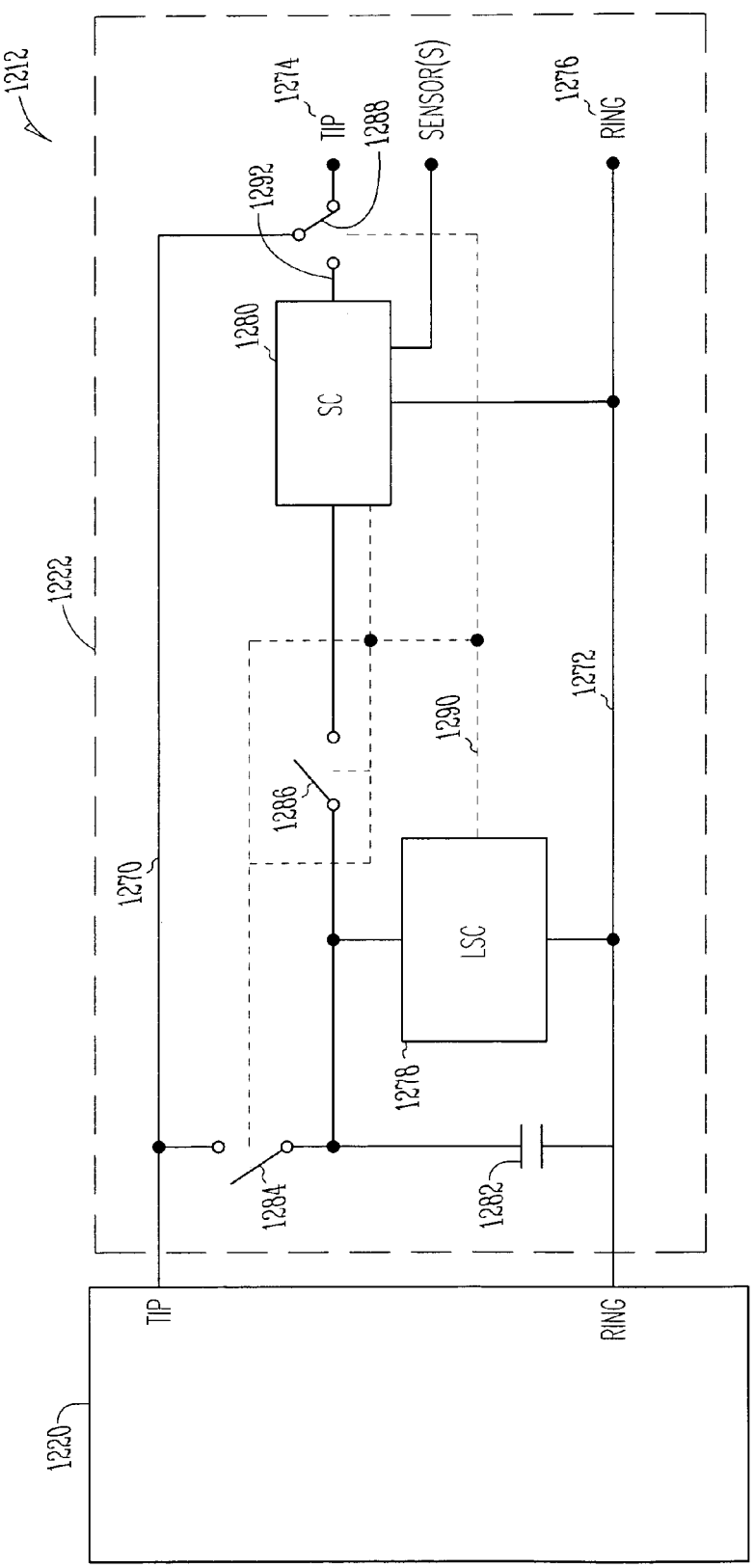

Referring to FIG. 12D, after a predetermined delay, the controller 1278 switches the third switch 1288 from the sensor circuit output 1292 back to the tip conductor 1274 and opens the second switch 1286 to disconnect power from the sensor circuit 1280. The pulse generator 1220 initiates the active discharge pulse (common to all pacing pulses). Should a different manufacturer's lead be used and the additional sensing capability not wanted, the pulse generator 1220 may be programmed to not perform this function.

Figure 12E:
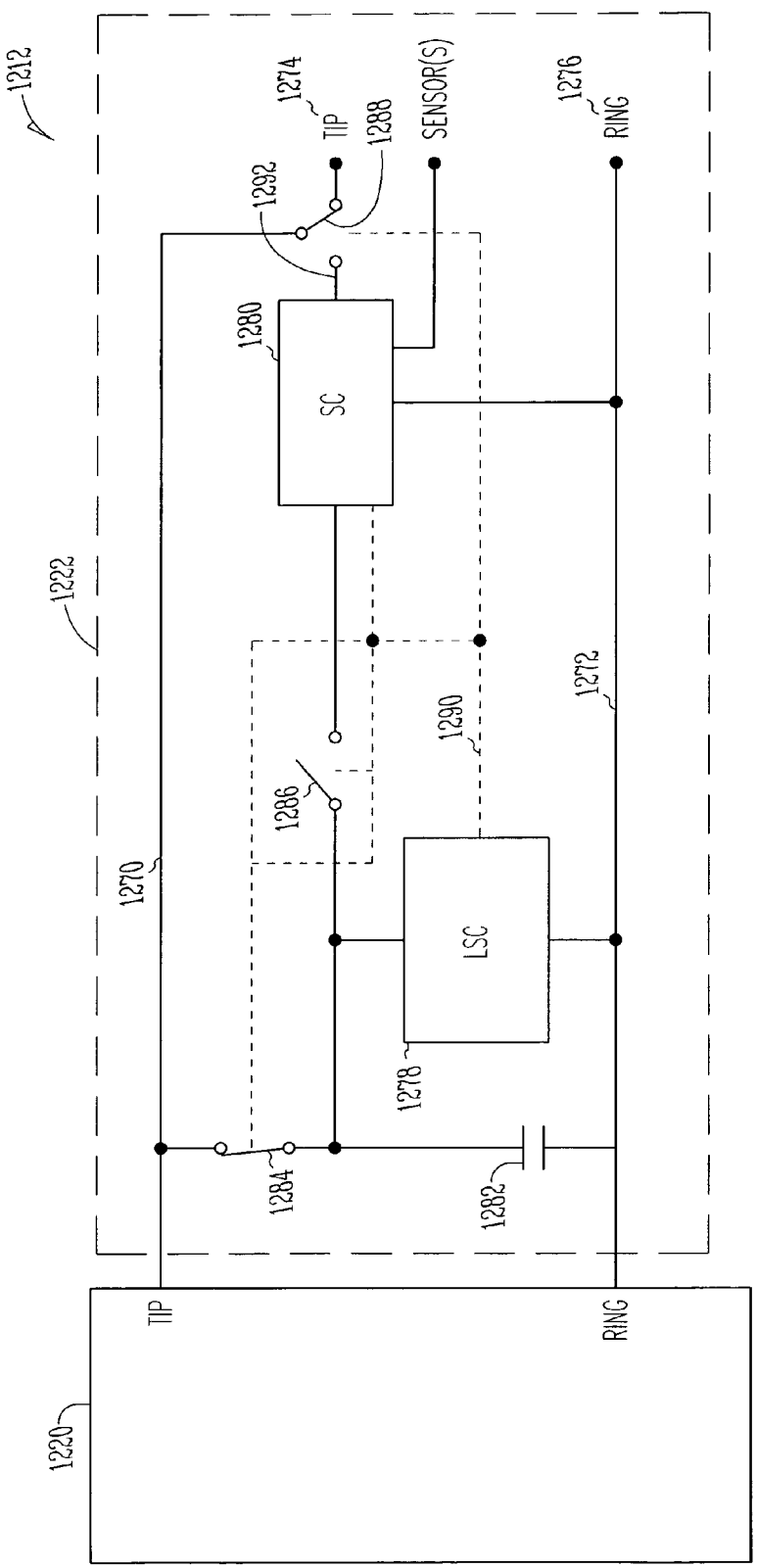

Referring to FIG. 12E, after a predetermined delay, the controller prepares for the next pacing pulse by closing the first switch 1284 to couple the capacitor 1282 in between the first and second conductors 1270 and 1272 such that a charge will be stored again in the capacitor 1282 during the next pulse. The cycle repeats on a regular interval or whenever a measurement is desired. According to one embodiment, should a pace not be needed because, for example, the heart is beating on its own, a subthreshold pacing pulse is used to initiate this sequence.

Figure 14:
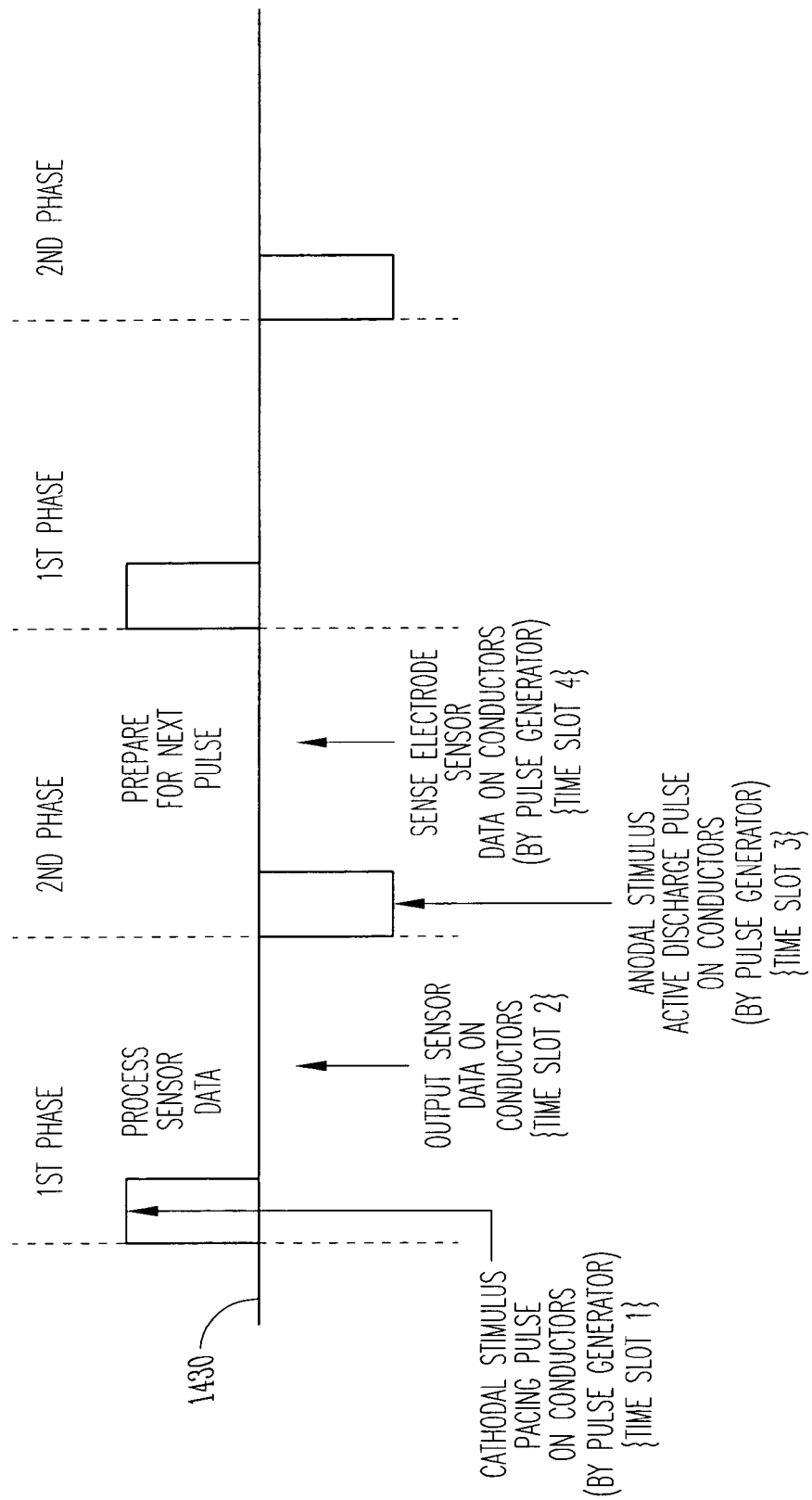
FIG. 14 illustrates one embodiment of a multiplex scheme according to the present subject matter.

FIG. 14 illustrates one embodiment of a multiplex scheme according to the present subject matter. A pacing pulse 1430 is illustrated with a potential between a tip electrode and a ring electrode. According to this embodiment, a pacing pulse has a cycle, or period, that includes a first phase and a second phase. The first phase of the pulse, i.e. cathodal stimulus, excites or depolarizes the heart. The depolarization of the heart causes a buildup of potential on the pacing electrode due to the ionic buildup necessary for charge transfer and heart tissue stimulation. If left alone, the electrode remains polarized and cannot be used for sensing until the electrode is depolarized. That is, a voltage remains on the electrode, and ions must be moved away from the surface of the electrode before the electrode can be used for sensing. The time required for the ions to move away from the surface can take quite a while if allowed to occur naturally through a slow diffusion of ions away from electrode. Therefore, in a second phase, an active discharge pulse, i.e. anodal stimulus, that is opposite in polarity with respect to the cathodal stimulus drives off the ions and depolarizes the electrode much quicker than the natural diffusion. After the ions have been removed by the active discharge pulse, the electrode can be used for sensing intrinsic electrical cardiac signals.

According to the illustrated embodiment, a pacing pulse is delivered from the pulse generator to the heart in a first time slot. As noted above, the sensor circuit processes the sensor data when it is powered. According to one embodiment, the sensor circuit is powered after the pacing pulse. According to another embodiment, the sensor circuit is powered continuously using charge stored in a sensor circuit capacitor. After the pacing pulse is delivered but before a subsequent active discharge pulse, the sensor circuit outputs the sensor data to the pulse generator in a second time slot. After the sensor circuit outputs the sensor data to the pulse generator, the active discharge pulse is delivered to depolarize the electrodes during a third time slot. After the active discharge pulse depolarizes the electrodes, the pulse generator is able to sense intrinsic electrical cardiac signals during a fourth time slot. According to one embodiment, each of these time slots are separated by predetermined delays. One of ordinary skill in the art will understand that FIG. 14 is an illustration of a multiplex scheme, and that the illustrated phases and pulses need not be evenly distributed or symmetrical.

Figure 15:
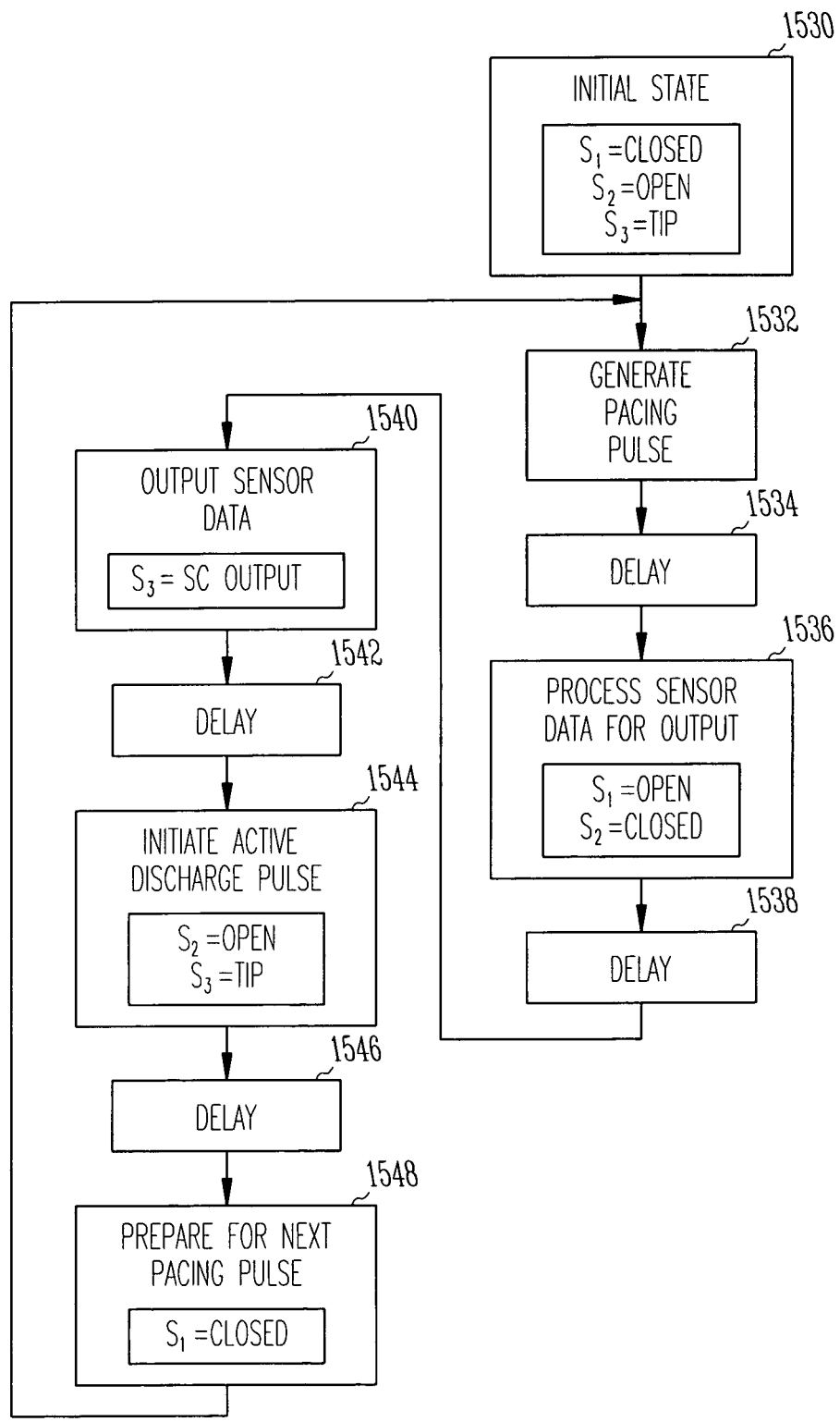
FIG. 15 illustrates one embodiment of a method according to the present subject matter.

FIG. 15 illustrates one embodiment of a method according to the present subject matter. According to this embodiment, an initial state is determined at 1530. For the schematic of the lead illustrated in FIG. 10, the initial state is when the first switch is closed, the second switch is open and the third switch is in contact with the tip electrode. The pulse generator generates a pacing pulse at 1532. Referring again to FIG. 14, the pacing pulse is generated in a first time slot in a pacing cycle. After a predetermined delay at 1534, the sensor circuit processes sensor data at 1536. For the schematic of the lead illustrated in FIG. 10, the first switch is open and the second switch is closed. After a predetermined delay at 1538, the sensor circuit outputs the sensor data to the pulse generator at 1540. Referring again to FIG. 14, the sensor data is output in a second time slot in the pacing cycle. For the schematic of the lead illustrated in FIG. 10, the third switch is in contact with the output of the sensor circuit. After a predetermined delay at 1542, the pulse generator initiates an active discharge pulse at 1544 to depolarize the electrodes from the pacing pulse. Referring again to FIG. 14, the active discharge pulse is generated in a third time slot in the pacing cycle. For the schematic of the lead illustrated in FIG. 10, the second switch is open and the third switch is in contact with the tip electrode. Another predetermined delay occurs at 1546. During this delay, the pulse generator is able to use the electrodes to sense intrinsic electrical cardiac signals. After the predetermined delay at 1546, the lead is prepared for the next pacing pulse at 1548. Referring again to FIG. 14, around or during the time in which the lead is prepared for the next pacing pulse, intrinsic cardiac signals are sensed in a fourth time slot. For the schematic of the lead illustrated in FIG. 10, the first switch maybe opened or closed during intrinsic sensing. The first switch closes before the next pacing pulse.

The present subject matter can be used to provide a number of additional sensing capabilities. One example of such additional sensing capabilities is a biochemical sensor. Other examples of additional sensing capabilities include an oxygen sensor, a carbon dioxide sensor, a pressure sensor and a temperature sensor. According to one embodiment, the sensors are designed to minimize the effects of encapsulation.

One desired sensing capability involves sensing catecholamines. Catecholamines are defined as any of various amines (as epinephrine, norepinephrine, and dopamine) that function as hormones or neurotransmitters or both. Catecholamines are produced by the adrenal medulla glands. Measurement can provide important clues in many cancers, often collectively termed neuruoendocrine tumors. Catecholamines are biochemicals that regulate cardiac activity through the nervous system. Catecholamines are chemically-similar small molecules that are derived from the amino acid tyrosine. The major catecholamines are dopamine, norepinephrine, and epinephrine (known also as adrenalin). Dopamine is a neurotransmitter (a chemical used to transmit impulses between cells), mainly in the brain. Norepinephrine is the primary neurotransmitter in the sympathetic nervous system and is also in the brain. Epinephrine is a neurotransmitter in the brain but is also a major hormone in the body.

The additional information obtained by the additional sensing capabilities on the lead is used to determine the appropriate therapy for a patient. Providing the additional sensing capabilities for a standard cardiac stimulus device lead without violating a header standard allows the pulse generator and the attachable leads of the cardiac stimulus device to be mixed and matched with those from other manufacturers. This flexibility increases the likelihood that physicians will choose to use cardiac stimulus devices with the added sensing capabilities.

Although specific embodiments have been illustrated and described herein, it will be appreciated by those of ordinary skill in the art that any arrangement which is calculated to achieve the same purpose may be substituted for the specific embodiment shown. This application is intended to cover any adaptations or variations of the present invention. It is to be understood that the above description is intended to be illustrative, and not restrictive. Combinations of the above embodiments, and other embodiments will be apparent to those of skill in the art upon reviewing the above description. The scope of the invention includes any other applications in which the above structures and fabrication methods are used. The scope of the invention should be determined with reference to the appended claims, along with the full scope of equivalents to which such claims are entitled.

What is claimed is:

1. A method for transmitting a pacing pulse from a pulse generator to an electrode and transmitting sensor data from a sensing circuit to the pulse generator using at least one switch and a shared conductor in a cardiac stimulus device lead, wherein the lead includes the sensing circuit external to the pulse generator and the sensing circuit is adapted to prepare the sensor data for output to the pulse generator, comprising:
    electrically connecting the shared conductor to the electrode, electrically disconnecting the shared conductor from the sensing circuit, and transmitting the pacing pulse using the shared conductor to the electrode when the shared conductor is electrically connected to the electrode and electrically disconnected from the sensing circuit; and
    electrically connecting the shared conductor to the sensing circuit and electrically disconnecting the shared conductor from the electrode, and transmitting the sensor data using the sensing circuit and the shared electrode when the shared conductor is electrically connected to the sensing circuit and electrically disconnected from the electrode.

2. The method of claim 1, wherein transmitting the pacing pulse includes periodically transmitting the pacing pulse.

3. The method of claim 1, wherein transmitting the pacing pulse and transmitting the sensor data includes using a time division multiplex scheme to transmit the pacing pulse and transmit the sensor data.

4. The method of claim 1, wherein the sensor data includes data sensed by a micro-electromechanical system.

5. The method of claim 1, wherein the sensor data includes sensed biochemical data.

6. The method of claim 1, wherein the sensor data includes sensed oxygen data.

7. The method of claim 1, wherein the sensor data includes sensed carbon dioxide data.

8. The method of claim 1, wherein the sensor data includes sensed catecholamines data.

9. The method of claim 1, wherein the sensor data includes sensed temperature data.

10. The method of claim 1, wherein the sensor data includes sensed pressure data.

11. The method of claim 1, further comprising storing charge in a capacitor during the pacing pulse, and using the charge stored in the capacitor to power the sensing circuit when the sensing circuit is electrically connected to the shared conductor.

12. A method for periodically transmitting a pacing pulse from a pulse generator to an electrode and transmitting sensor data from a sensing circuit to the pulse generator using a shared conductor in a cardiac stimulus device lead, comprising:
    transmitting the pacing pulse to the electrode using the shared conductor during a first time slot of a pulse period, including electrically connecting the shared conductor to the electrode and electrically disconnecting the shared conductor from the sensing circuit in preparation to transmit the pacing pulse;
    transmitting sensor data acquired during a preceding pulse period from the sensing circuit to the pulse generator using the shared conductor during a second time slot of the pulse period, including electrically connecting the shared conductor to the sensing circuit and electrically disconnecting the shared conductor from the electrode in preparation to transmit the previously-acquired sensor data;
    transmitting an active discharge pulse to the electrode using the shared conductor during a third time slot of the pulse period, including electrically connecting the shared conductor to the electrode and electrically disconnecting the shared conductor from the sensing circuit in preparation to transmit the pacing pulse; and
    acquiring sensor data using the electrode during a fourth time slot of the pulse period, including storing the sensor data in the sensor circuit.

13. The method of claim 12, further comprising storing charge in a capacitor during the pacing pulse, and using the charge stored in the capacitor to power the sensing circuit when the sensing circuit is electrically connected to the shared conductor.

14. The method of claim 12, further comprising sensing the pacing pulse, wherein transmitting sensor data is response to detecting the pacing pulse.

15. A method, comprising:
    generating a pacing pulse for transmission on a cardiac stimulus device lead;
    processing sensor data at the lead using a sensor circuit external to a pulse generator, wherein processing the sensor data includes preparing the sensor data for output to the pulse generator;

outputting sensor data for transmission on the lead using at least one switch;
initiating an active discharge pulse for transmission on the lead; and
preparing for a subsequent pacing pulse.

16. The method of claim 15, wherein outputting sensor data occurs after generating a pacing pulse and before initiating an active discharge pulse.

17. The method of claim 15, wherein outputting sensor data occurs in a predetermined time slot with respect to generating a pacing pulse.

18. The method of claim 15, wherein outputting sensor data occurs in response to receiving an electrical signal.

19. The method of claim 15, wherein outputting sensor data occurs in response to detecting the pacing pulse.

20. The method of claim 15, further comprising:
providing a first predetermined delay after generating a pacing pulse and prior to processing sensor data;
providing a second predetermined delay after processing sensor data and prior to outputting sensor data;
providing a third predetermined delay after outputting sensor data and prior to initiating an active discharge pulse; and
providing a fourth predetermined delay after initiating an active discharge pulse and prior to preparing for the next pacing pulse.

21. The method of claim 15, wherein generating a pacing pulse occurs during an initial state that is formed by bleeding a pacing pulse to store a charge on a capacitor, disconnecting a sensor circuit from the charge stored on the capacitor, and coupling a first conductor to a first electrode to deliver the pacing pulse to the heart.

22. The method of claim 21, wherein processing sensor data includes disconnecting the capacitor from a first conductor and providing power to the sensing circuit from the charge stored on the capacitor.

23. The method of claim 22, wherein disconnecting the capacitor from a first conductor includes opening a first switch positioned between the capacitor and the first conductor, and providing power to the sensing circuit includes closing a second switch positioned between the capacitor and the sensing circuit.

24. The method of claim 15, wherein processing sensor data includes processing sensed biochemical data.

25. The method of claim 15, wherein processing sensor data includes processing sensed oxygen data.

26. The method of claim 15, wherein processing sensor data includes processing sensed carbon dioxide data.

27. The method of claim 15, wherein processing sensor data includes processing sensed catecholamines data.

28. The method of claim 15, wherein processing sensor data includes processing sensed temperature data.

29. The method of claim 15, wherein processing sensor data includes processing sensed pressure data.

30. The method of claim 15, wherein outputting sensor data includes coupling an output of the sensor circuit to a first conductor.

31. The method of claim 30, wherein outputting sensor data includes actuating a third switch to couple the output of the sensor circuit to the first conductor.

32. The method of claim 15, wherein initiating an active discharge pulse includes disconnecting a sensor circuit from a charge stored on a capacitor, and coupling a first conductor to a first electrode.

33. The method of claim 32, wherein disconnecting a sensor circuit from the charge stored on the capacitor includes opening a second switch to disconnect the sensor circuit from the charge stored on the capacitor, and actuating a third switch to couple the first conductor to the first electrode.

34. The method of claim 15, wherein preparing for a subsequent pacing pulse includes closing a first switch to charge a capacitor by bleeding power from a subsequent pacing pulse.

35. The method of claim 15, further comprising sensing intrinsic cardiac electrical signals after initiating an active discharge pulse.

36. The method of claim 15, wherein the pacing pulse is generated by a pulse generator, then the sensor data is output by a sensing circuit, then the active discharge pulse is initiated by the pulse generator, and then an intrinsic cardiac electrical signal is sensed by the pulse generator using lead electrodes.

* * * * *